United States Patent
Neumann

(10) Patent No.: US 11,562,828 B2
(45) Date of Patent: Jan. 24, 2023

(54) METHODS AND SYSTEMS FOR CUSTOMIZING TREATMENTS

(71) Applicant: KPN Innovations, LLC, Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 16/727,099

(22) Filed: Dec. 26, 2019

(65) Prior Publication Data
US 2021/0202088 A1 Jul. 1, 2021

(51) Int. Cl.
*G16H 50/20* (2018.01)

(52) U.S. Cl.
CPC .................... *G16H 50/20* (2018.01)

(58) Field of Classification Search
CPC ........ G16H 50/20; G16H 50/50; G16H 40/67; G16H 10/60; G16H 15/00; G16H 50/30; G16H 50/70; G16H 20/13; G16H 20/30; G16H 40/63; G16H 30/20; G16H 50/80; G16H 20/60; G16H 20/00; G16H 20/10; G16H 20/70; G16H 30/40; G06Q 40/08; G06Q 50/22; G06Q 10/00; G06Q 10/06
USPC ........................................................ 705/2–3
See application file for complete search history.

(56) References Cited

U.S. PATENT DOCUMENTS

| | | | |
|---|---|---|---|
| 10,559,386 B1 * | 2/2020 | Neumann | G06N 20/20 |
| 2005/0176057 A1 * | 8/2005 | Bremer | A61K 31/00 435/6.16 |
| 2011/0119212 A1 * | 5/2011 | De Bruin | A61B 5/00 706/12 |
| 2014/0279746 A1 | 9/2014 | De Bruin et al. | |
| 2016/0302671 A1 * | 10/2016 | Shariff | G16H 50/50 |
| 2016/0364545 A1 | 12/2016 | Das et al. | |
| 2018/0102190 A1 | 4/2018 | Hogue et al. | |
| 2018/0150608 A1 | 5/2018 | Kim et al. | |
| 2018/0166174 A1 | 6/2018 | Lewis | |

(Continued)

FOREIGN PATENT DOCUMENTS

| | | | |
|---|---|---|---|
| WO | WO-2015/118529 | * | 8/2015 |
| WO | 2019211089 | | 11/2019 |

OTHER PUBLICATIONS

Gaudillo et al., Machine Learning Approach to Single Nucleotide Polymorphism-based Asthmaprediction, PLoS ONE, Dec. 4, 2019, vol. 14 issue 12, PLOS ONE.

(Continued)

*Primary Examiner* — Joy Chng
(74) *Attorney, Agent, or Firm* — Caldwell Intellectual Property Law

(57) ABSTRACT

A system for customizing treatments. The system includes a computing device configured to record a user biological extraction containing an element of user physiological data. The computing device is configured to receive condition state training data and generate a condition state model utilizing a first machine-learning algorithm. The computing device is configured to calculate a condition state label using the condition state model. The computing device is configured to select a treatment model utilizing the condition state label. The computing device is configured to generate a treatment model and output a plurality of treatments utilizing the treatment model.

18 Claims, 6 Drawing Sheets

(56) References Cited

U.S. PATENT DOCUMENTS

| | | | |
|---|---|---|---|
| 2018/0315494 A1* | 11/2018 | Kolde | G16H 15/00 |
| 2019/0019581 A1 | 1/2019 | Vaughan et al. | |
| 2019/0043610 A1* | 2/2019 | Vaughan | G16H 50/70 |
| 2019/0096526 A1 | 3/2019 | Hirsch et al. | |
| 2019/0216350 A1 | 7/2019 | Sullivan et al. | |
| 2019/0258962 A1* | 8/2019 | Sreekumari | G06N 20/10 |
| 2019/0272922 A1* | 9/2019 | Albright | G06K 9/00536 |
| 2019/0279767 A1 | 9/2019 | Bates | |
| 2019/0341152 A1 | 11/2019 | Mellem et al. | |
| 2019/0362846 A1* | 11/2019 | Vodencarevic | G06K 9/2063 |
| 2019/0371450 A1 | 12/2019 | Bin et al. | |
| 2019/0371463 A1 | 12/2019 | Asthana et al. | |

OTHER PUBLICATIONS

International Search Report; PCT/US2020/066883; dated Mar. 8, 2021; Authorized Officer: Blaine R. Copenheaver.

* cited by examiner

METHODS AND SYSTEMS FOR CUSTOMIZING TREATMENTS

FIELD OF THE INVENTION

The present invention generally relates to the field of artificial intelligence. In particular, the present invention is directed to methods and systems for customizing treatments.

BACKGROUND

Frequently, treatments are arbitrarily recommended based on current trends and stale literature. On occasion, uninformed treatment selection and implementation leads to adverse effects that create further harm as opposed to solving an underlying problem. Currently, there lacks measures that can detect and recommend treatments that are customized and unique to each individual.

SUMMARY OF THE DISCLOSURE

In an aspect, a system for customizing treatments includes a computing device the computing device designed and configured to record a user biological extraction containing an element of user physiological data. The computing device is further configured to receive condition state training data wherein the condition state training data further comprises a plurality of physiological data sets and a plurality of correlated condition state labels. The computing device is further configured to generate a condition state model, using the element of user physiological data and the condition state training data, and using a first machine-learning algorithm, wherein the condition state model utilizes physiological data as inputs and outputs condition state labels. The computing device is further configured to calculate a condition state label for the element of user physiological data using the condition state model. The computing device is further configured to select a treatment training set utilizing the condition state label wherein the treatment training set further comprises a plurality of condition state labels and a plurality of correlated treatments. The computing device is further configured to generate a treatment model, using a second machine-learning algorithm, the condition state label and the treatment training set, wherein the treatment model utilizes condition state labels as inputs and outputs treatments. The computing device is further configured to output a plurality of treatments utilizing the treatment model.

In an aspect, a method of customizing treatments includes recording by a computing device a user biological extraction containing an element of user physiological data. The method includes receiving by the computing device condition state training data wherein the condition state training data further comprises a plurality of physiological data sets and a plurality of correlated condition state labels. The method includes generating by the computing device a condition state model, using the element of user physiological data and the condition state training data, and using a first machine-learning algorithm, wherein the condition state model utilizes physiological data as inputs and outputs condition state labels. The method includes calculating by the computing device a condition state label for the element of user physiological data using the condition state model. The method includes selecting by the computing device a treatment training set utilizing the condition state label wherein the treatment training set further comprises a plurality of condition state labels and a plurality of correlated treatments. The method includes generating by the computing device a treatment model, using a second machine-learning algorithm, the condition state label and the treatment training set, wherein the treatment model utilizes condition state labels as inputs and outputs treatments. The method includes outputting by the computing device a plurality of treatments utilizing the treatment model.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, embodiments disclosed herein utilize a human subject's biological extraction to propose suggested treatments. Suggested treatments are determined to be compatible and uniquely suggested for each human subject.

Figure 1:
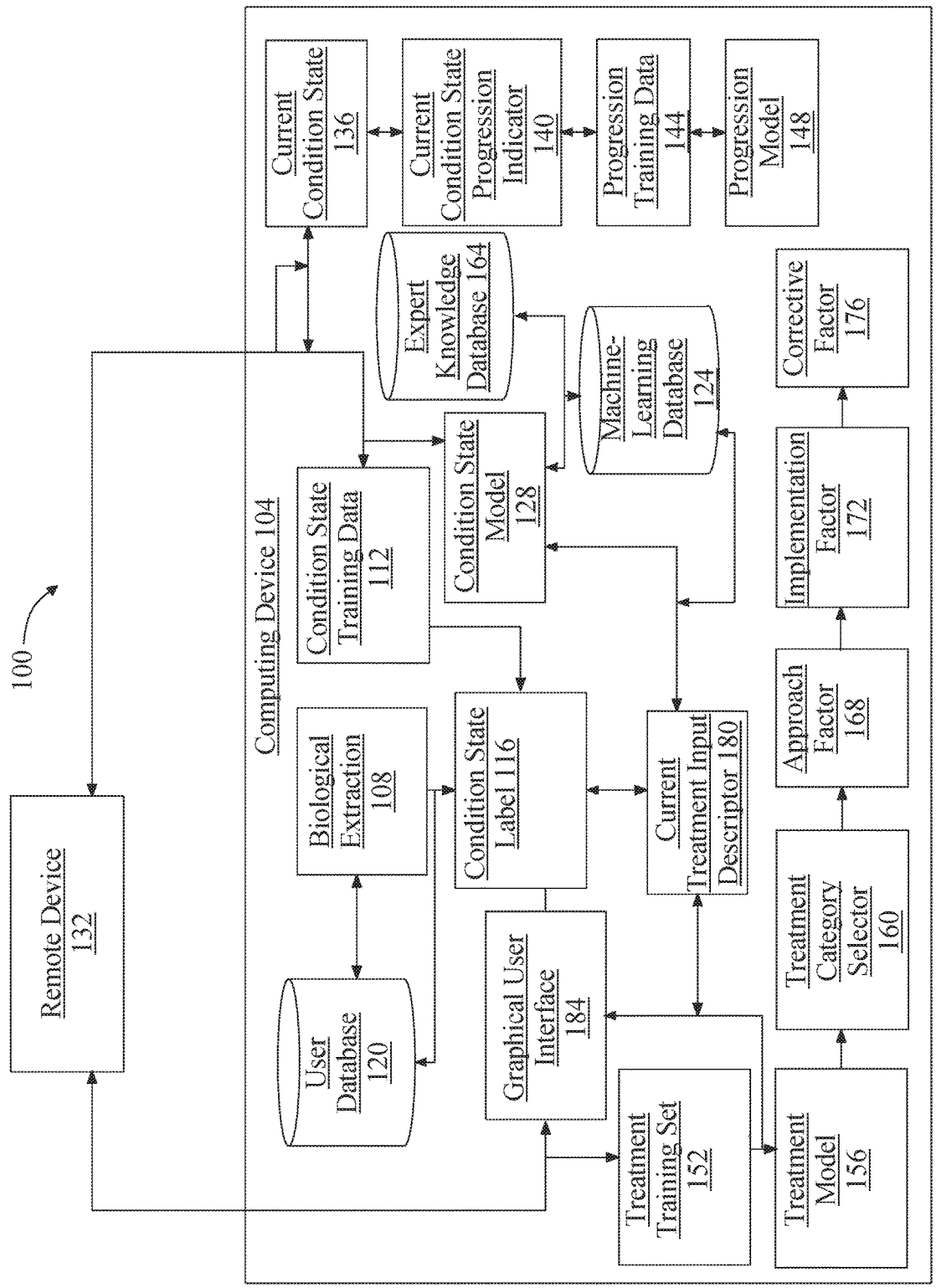
FIG. 1 is a block diagram illustrating an exemplary embodiment of a system for customizing treatments.

Referring now to FIG. 1, an exemplary embodiment of a system 100 for customizing treatments is illustrated. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices 104 of computing device 104, which may operate in parallel, in series, redundantly, or in any other manner used for distribution of tasks or memory between computing devices 104. Computing device 104 may be implemented using a "shared nothing" architecture in which data is cached at the worker; in an embodiment, this may enable scalability of system 100 and/or computing device 104.

Still referring to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to record a user biological extraction 108 containing at least an element of user physiological data. A "biological extraction" as used in this disclosure includes at least an element of user physiological data. As used in this disclosure, "physiological data" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. A user biological extraction may contain a plurality of elements of user physiological data, such as for example several biomarkers obtained from a blood test or multiple biomarkers obtained from a saliva sample. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C(HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing module as described in this disclosure.

Still referring to FIG. 1, physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data may include, without limitation any result of any medical test, physiological assessment, cognitive assessment, psychological assessment, or the like. System 100 may receive at least a physiological data from one or more other devices after performance; system 100 may alternatively or additionally perform one or more assessments and/or tests to obtain at least a physiological data, and/or one or more portions thereof, on system 100. For instance, at least physiological data may include or more entries by a user in a form or similar graphical user interface 184 116 object; one or more entries may include, without limitation, user responses to questions on a psychological, behavioral, personality, or cognitive test. For instance, at least a server 104 may present to user a set of assessment questions designed or intended to evaluate a current state of mind of the user, a current psychological state of the user, a personality trait of the user, or the like; at least a server 104 may provide user-entered responses to such questions directly as at least a physiological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, physiological data may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, physiological data may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, firmicutes, Bacteroidetes, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, *cryptosporidium* EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *campylobacter* species, *Clostridium difficile, cryptosporidium* species, *Cyclospora cayetanensis, Cryptosporidium* EIA, *Dientamoeba fragilis, Entamoeba histolytica, Escherichia coli, Entamoeba histolytica, Giardia, H. pylori, Candida albicans, Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example Firmicutes species, Bacteroidetes species, Proteobacteria species, Verrumicrobia species, Actinobacteria species, Fusobacteria species, Cyanobacteria species and the like. Archaea may include methanogens such as *Methanobrevibacter* smithies' and Methanosphaera stadtmanae. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as Ackerman's muciniphila, Anaerotruncus colihominis, bacteriology, *Bacteroides vulgates', Bacteroides-Prevotella, Barnesiella* species, *Bifidobacterium longarm, Bifidobacterium* species, *Butyrivbrio crossotus, Clostridium* species, *Collinsella aerofaciens*, fecal color, fecal consistency, *Coprococcus eutactus, Desulfovibrio piger, Escherichia coli, Faecalibacterium prausnitzii*, Fecal occult blood, Firmicutes to Bacteroidetes ratio, *Fusobacterium* species, *Lactobacillus* species, *Methanobrevibacter smithii*, yeast minimum inhibitory concentration, bacteria minimum inhibitory concentration, yeast mycology, fungi mycology, *Odoribacter* species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen based breath tests, fructose based breath tests. *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vaso-dilation and vaso-constriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fulness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androstereone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1. Persons skilled in the art, upon reviewing the entirety of this disclosure, will be aware of various additional examples of physiological state data that may be used consistently with descriptions of systems and methods as provided in this disclosure.

With continued reference to FIG. 1, physiological data may be obtained from a physically extracted sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Physiological data may be obtained from a physically extracted sample. A physical sample may include a signal from a sensor configured to detect physiological data of a user and record physiological data as a function of the signal. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of system 100 or may be a separate device in communication with system 100.

With continued reference to FIG. 1, computing device 104 is configured to receive condition state training data 112. "Condition state training data," as used in this disclosure, is training data that contains a plurality of physiological data sets and a plurality of correlated condition state label. Training data, as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device 104 may correlate any input data as described in this disclosure to any output data as described in this disclosure.

With continued reference to FIG. 1, a "condition state label," as used in this disclosure, is an element of data identifying and/or describing a current, incipient, or probable future medical condition affecting a human being; medical condition may include a particular disease, one or more symptoms associated with a syndrome, a syndrome, and/or any other measure of current or future health and/or heathy aging. A condition state label 116 may identify a disease including any condition that impairs the normal function of the human body. A condition state label 116 may identify the absence of a disease or condition. For example, a condition state label 116 may identify a disease such as an infection, or a genetic disease. In yet another non-limiting example, a condition state label 116 may identify that a user is free and clear of disease. A condition state label 116 may identify an acquired disease such as one that begins at some point during one's lifetime, as opposed to disease already present at birth. For example, a condition state label 116 may identify an acquired disease such as viral cardiomyopathy. A condition state label 116 may identify a congenital disease that may be present at birth such as a baby born with human immune deficiency virus (HIV). A congenial disease may include an inherited genetic disease or disorder such as for example cystic fibrosis, marfan syndrome, fragile X syndrome, or hemochromatosis. A condition state label 116 may identify an acute disease such as one that is of a short-term nature such as a urinary tract infection (UTI). A condition state label 116 may identify a chronic condition and/or chronic disease such as hypertension. A condition state label 116 may identify a genetic disorder and/or genetic disease that may be caused by one or more genetic mutations. For example, a condition state label 116 may identify a genetic disease such as Huntington's disease. A condition state label 116 may identify a hereditary and/or inherited disease such as familial hypercholesterolemia. A condition state label 116 may identify an iatrogenic disease caused by medical intervention such as a side effect of a treatment or as an inadvertent outcome. For example, a condition state label 116 may identify a prescription drug adverse effect such as an antibiotic that causes excessive diarrhea or vertigo experienced as a side effect from brain surgery. A condition state label 116 may identify idiopathic disease such as disease having an unknown cause or source. For example, a condition state label 116 may identify an idiopathic disease such as multiple sclerosis or diabetes mellitus type 1. A condition state label 116 may identify an incurable disease such as a disease that is terminal or a disease that has to be treated for the rest of a user's life. A condition state label 116 may identify primary disease that is due to a root cause illness such as a bacterial infection. A condition state label 116 may identify secondary disease that is a sequela and/or complication of a prior, causal disease such as for example, a bacterial infection that develops at the site of a burn. A condition state label 116 may identify a terminal disease such as a disease that is expected to have the inevitable result of death. A condition state label 116 may identify a disorder that may include a functional abnormality and/or disturbance. For example, a condition state label 116 may identify a mental disorder, physical disorder, genetic disorder, emotional disorder, behavior disorder, functional disorder and the like. A condition state label 116 may identify a medical condition that includes all diseases, lesions, disorders, and/or nonpathological conditions that require medical treatment. A condition state label 116 may identify a syndrome that may include an association of several medical signs and symptoms that occur together. For example, a condition state label 116 may identify a syndrome such as Down syndrome, Parkinsonian syndrome, acute coronary syndrome and the like. A condition state label 116 may identify predisease, which includes any subclinical and/or prodromal presentation of a disease. For example, a condition state label 116 may identify predisease such as prediabetes or prehypertension. A condition state label 116 may identify an affected body system such as the renal system when a disease or condition affects the kidneys.

With continued reference to FIG. 1, computing device 104 may receive condition state training data 112 generated from one or more user entries. In an embodiment, computing device 104 may receive previously collected user data to generate condition state training data that includes a plurality of physiological data obtained from user entries and a plurality of correlated user condition state labels obtained from user entries. In an embodiment, one or more biological extraction 108, one or more elements of user physiological data, and/or one or more condition state label 116 may be stored in a user database 120. User database 120 may be implemented, without limitation, as a relational database, a key-value retrieval datastore such as a NOSQL database, or any other form or structure for use as a datastore that a person skilled in the art would recognize as suitable upon review of the entirety of this disclosure. Computing device 104 may retrieve previous user entries to generate condition state training data 112 based on one or more previous user entries.

With continued reference to FIG. 1, computing device 104 is configured to generate a condition state model utilizing one or more machine-learning processes. Condition state model is a machine-learning model, which as used herein, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

With continued reference to FIG. 1, a machine learning process, also referred to as a machine-learning algorithm, is a process that automatedly uses training data and/or a training set as described above to generate an algorithm that will be performed by a computing device 104 and/or module to produce outputs given data provided as inputs; this is in contrast to a non-machine learning software program where the commands to be executed are determined in advance by a user and written in a programming language.

Continuing to refer to FIG. 1, machine-learning algorithms may be implemented using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure, Still referring to FIG. 1, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

With continued reference to FIG. 1, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data.

Still referring to FIG. 1, machine-learning algorithms may include supervised machine-learning algorithms. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised machine-learning process may include a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs.

With continued reference to FIG. 1, supervised machine-learning processes may include classification algorithms, defined as processes whereby a computing device 104 derives, from training data, a model for sorting inputs into categories or bins of data. Classification may be performed using, without limitation, linear classifiers such as without limitation logistic regression and/or naive Bayes classifiers, nearest neighbor classifiers including without limitation k-nearest neighbors classifiers, support vector machines, decision trees, boosted trees, random forest classifiers, and/or neural network-based classifiers.

Still referring to FIG. 1, machine learning processes may include unsupervised processes. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like. Unsupervised machine-learning algorithms may include, without limitation, clustering algorithms and/or cluster analysis processes, such as without limitation hierarchical clustering, centroid clustering, distribution clustering, clustering using density models, subspace models, group models, graph-based models, signed graph models, neural models, or the like. Unsupervised learning may be performed by neural networks and/or deep learning protocols as described above.

With continued reference to FIG. 1, computing device 104 uses an element of user physiological data and condition state training data 112, in combination with a first machine-learning algorithm to utilize physiological data as inputs and output condition state label 116. First machine-learning algorithm includes any of the machine-learning algorithms as described herein. In an embodiment, one or more machine-learning processes such as condition state model, condition state label 116, and/or condition state training data may be stored in machine-learning database 124. Machine-learning database 124 may be implemented as any data structure suitable for use as user database 120 as described above in more detail.

With continued reference to FIG. 1, computing device 104 is configured to calculate a condition state label 116 for an element of user physiological data using a condition state model 128. Condition state label 116 includes any of the condition state label 116 as described above. A "condition state model," as used in this disclosure, is a machine-learning model that utilizes physiological data as inputs and outputs condition state label. Generating a condition state model may include performing a series of one or more calculations, algorithms, and/or equations. Condition state model may include any of the machine-learning models as described herein. In an embodiment, condition state model may include a classification algorithm, defined as processes whereby a computing device 104 derives, from training data, a model for sorting inputs into categories or bins of data. Classification may be performed using, without limitation, linear classifiers such as without limitation logistic regression and/or naive Bayes classifiers, nearest neighbor classifiers including without limitation k-nearest neighbors classifiers, support vector machines, decision trees, boosted trees, random forest classifiers, and/or neural network-based classifiers.

With continued reference to FIG. 1, system 100 may include a remote device 132. Remote device 132 may include without limitation, a display in communication with computing device 104, where a display may include any display as described herein. Remote device 132 may include an additional computing device, such as a mobile device, laptop, desktop, computer and the like. Remote device 132 may be configured to transmit and/or receive one or more inputs from computing device 104 utilizing any network methodology as described herein. Remote device 132 may be operated by a user which may include any human subject. Remote device 132 may be operated by an informed advisor, which may include any healthcare provider such as for example, a functional medicine physician, a nurse practitioner, a yoga teacher, a fitness instructor, a health coach, a reiki master, a massage therapist, an acupuncturist and the like.

With continued reference to FIG. 1, computing device 104 may receive from a remote device 132 a description of a current condition state 136. A "current condition state," as used in this disclosure, is data describing any current, incipient, or probable future medical condition that a user has been diagnosed with. A current condition state 136 may include a description of a current disease state such as rheumatoid arthritis that a use was diagnosed with three years back. A current condition state 136 may include a description of a probable future medical condition that a user may be diagnosed with in the future such as type 2 diabetes mellitus due to a user's current diagnosis of prediabetes. A current condition state may be generated by a user such as when a user enters one or more current condition state 136 that the user was previously diagnosed with and self-reports. A current condition state 136 may be generated by an informed advisor, such as when a user's functional medicine physician may generate a current condition state 136 at a remote device 132 and transmit the current condition state 136 to computing device 104. In an embodiment, a current condition state 136 may be stored within user database 120. Computing device 104 may utilize a description of a current condition state 136 received from a remote device 132 to calculate a condition state label 116 to contain a current condition state progression indicator 140. A "current condition state progression indicator," as used in this disclosure, is a description of how far progressed a current condition state 136 is. Progression may include one or more classifications that indicate how advanced a particular condition state may be based on factors such as etiology, pathophysiology, and/or severity. Progression may indicate if a particular disease and/or condition is acute, such as when a disease may be short-lived such as the common cold. Progression may indicate if a particular disease and/or condition is chronic, such as a disease that lasts for an extended duration, such as more than six months. Progression may indicate a clinical disease, such as a disease that has clinical consequences. For example, acquired immune deficiency syndrome (AIDS), may be a clinical disease state of human immune deficiency virus (HIV). Progression may indicate a flare-up, such as when there is a recurrence of symptoms of a disease or condition, and/or when there is an onset of more severe symptoms. Progression may indicate a disease and/or condition whose typical natural course is worsening such as multiple sclerosis that is progressing to an extent where a user can no longer walk without the use of a cane. Progression may indicate a refractory disease, such as a disease that resists treatment. Progression may indicate a subclinical disease, such as a silent disease that occurs before symptoms are first noticed. Progression may indicate a terminal phase, such as a disease where a user will die soon, such as terminal cancer. Progression may indicate an extent of disease such as a localized disease that affects only one part of the body, such as athlete's foot or an eye infection. Progression may indicate disseminated disease that has spread to other areas of the body, such as cancer. Progression may indicate systemic disease, such as a disease that affects the entire body such as influenza or high blood pressure. Progression may indicate diseases that may be classified by involved organ system. Progression may indicate cause, such as a disease caused by lifestyle and behavioral choices. Progression may indicate infection rate of disease such as transmission of communicable disease. Computing device 104 may utilize a condition state label 116 containing a current condition state progression indicator 140 to select a treatment training set 152 and a treatment training model as described below in more detail.

With continued reference to FIG. 1, condition state progression indicator may be generated utilizing a machine-learning process. Computing device 104 may receive progression training data 144. "Progression training data," as used in this disclosure, is training data that contains a plurality of physiological data sets and a plurality of correlated progression indicators. "Progression indicators" as used in this disclosure, are a description of how far progressed a current condition state 136 is. Progression indicators may include any data suitable for use as condition state progression indicator. Computing device 104 generates a progression model 148 using a machine-learning algorithm, the element of user physiological data, and the progression training data 144. Machine-learning algorithm includes any of the machine-learning algorithms as described herein. A "progression model," as used in this disclosure, is a machine-learning model that utilizes physiological data as inputs and outputs progression indicators. A progression model 148 may include performing a series of one or more calculations, algorithms, and/or equations. Computing device 104 calculates a condition state progression indicator utilizing a progression model 148. Progression model 148 may be generated by calculating one or more machine-learning algorithms, including any of the machine-learning algorithms as described herein.

With continued reference to FIG. 1, computing device 104 is configured to select a treatment training set 152 and utilizing a condition state label 116. A "treatment training set," as used in this disclosure, is a set of training data that contains a plurality of condition state labels 116 and a plurality of correlated treatments. A "treatment," as used in this disclosure, is any process given, prescribed, and/or recommended for a condition which may be identified using any condition state label 116. A treatment may include a medication including for example any prescription and/or non-prescription medications such as vitamins, herbs, supplements, homeopathic remedies, nutraceuticals, minerals, prescription medications dispensed at a pharmacy, and the like. A treatment may include a program such as for example a fitness program containing recommended exercises and exercise routines. A treatment may include a meditation program such as for example a meditation practice to be implemented into a user's everyday life routine. A treatment may include a food program such as for example recommended foods to consume and not consume as well as one or more meal plans. A treatment may include one or more procedures including for example surgical and/or non-surgical procedures. A treatment may include a spiritual practice which may be associated with a particular religion such as Christianity for example. A treatment may include one or more psychological treatments including for example therapy sessions, behavior modifications, and counseling services.

With continued reference to FIG. 1, computing device 104 may select a treatment training set 152 and/or a treatment model 156 that corresponds to condition state label 116. A "treatment model," as used in this disclosure, is a machine-learning model that utilizes a condition state label 116 as an input and outputs treatments. Generating a treatment model 156 may include performing a series of one or more calculations, algorithms, and/or equations. Treatment model 156 may include calculating one or more machine-learning algorithms, including any of the machine-learning algorithms as described above. In an embodiment, treatment training set 152 and/or a treatment model 156 may contain a label identifying which conditions, identified by condition state label 116, treatment training set 152 and/or treatment model 156 may be utilized for. Computing device 104 may identify treatment training set 152 and/or treatment model 156 intended for an output condition state label 116 and select a treatment training set 152 and/or treatment model 156 that hews most closely to a condition state label 116. For example, computing device 104 may identify a first treatment training set 152 and a first treatment model 156 that may be utilized for autoimmune conditions such as multiple sclerosis, ulcerative colitis, Crohn's disease, and hashimoto's thyroiditis; and a second treatment training set 152 and a second treatment model 156 that may be utilized for ulcerative colitis. Computing device 104 may select second treatment training set 152 and second treatment model 156 for a condition state label 116 that contains ulcerative colitis, as second treatment training set 152 and second treatment model 156 are specifically intended for ulcerative colitis, while first treatment training set 152 and first treatment model 156 are intended more broadly for autoimmune conditions. In an embodiment, treatment training set 152 and treatment model 156 may be stored within machine-learning database 124. In an embodiment, treatment model may be precalculated and stored within a database and ready to be generated immediately.

With continued reference to FIG. 1, computing device 104 may select a treatment training set 152 and/or a treatment model 156 by calculating a treatment category selector 160. A "treatment category selector," as used in this disclosure, is a description of a particular category of treatment to be implemented and/or recommended for a particular condition identified from a condition state label 116. A category of treatment may include a class of treatments having shared characteristics. A category may include for example fitness treatments which may include further sub-categories such as cardiovascular fitness treatment, strength and toning fitness treatment, endurance fitness treatment, relaxation fitness treatment, meditative fitness treatment and the like. Other categories of treatments may include nutrition treatments, alternative medicine treatments, spiritual treatments, behavior modification treatments, prescription treatments, non-prescriptive treatments, coaching treatments, and the like. In an embodiment, certain conditions identified with condition state label 116 may respond more favorable to a particular treatment category selector 160 than another. For instance and without limitation, prediabetes may respond more favorably to condition treatment selectors that include fitness and nutritional treatment, while a gambling addiction may respond more favorably to behavior modification treatment and psychiatric treatment. Computing device 104 may calculate a treatment category selector 160 based on one or more inputs stored within user database 120 that may be generated by preferences input by a user and/or informed advisor. For example, a user may indicate that he prefers fitness treatments over nutritional treatments or that he does not enjoy specific forms of exercise that include biking and running.

With continued reference to FIG. 1, computing device 104 may calculate a treatment category selector 160. Computing device 104 may calculate a treatment category selector 160 by multiplying an approach factor multiplied by an implementation factor multiplied by a corrective factor. An output calculated treatment category selector 160 may be utilized to select a particular treatment training set 152 and/or treatment model 156. In an embodiment, a calculated treatment category selector 160 may output a numerical score with each factor utilized to calculate treatment category selector 160 being given an individual score that is multiplied together to produce a final output containing a calculated treatment category selector 160. The total final output calculated numerical value may be utilized to select a treatment training set 152 and/or treatment model 156 based on numerical ranges that may be assigned to treatment training set 152 and/or treatment model 156 based on expert input. Expert input may be provided and stored in an expert knowledge database 164. Expert knowledge database 164 may be implemented as any data structure suitable for use as user database 120 as described above. Expert knowledge database 164 may include expert input obtained from expert inputs such as top medical experts, journal articles, scientific studies and the like as described in more detail below. An "approach factor," as used in this disclosure, is a factor that indicates an acceptable treatment approach by experts for a given condition identified with a condition state label 116. An approach factor 168 may include a standard endorsed by one or more treatment guidelines. This may include for example diagnostic and/or treatment processes that a healthcare provider may follow for a certain type of patient, illness, and/or clinical circumstance. A standard may be endorsed by one or more medical associations and/or organizations such as for example, THE INSTITUTE FOR FUNCTIONAL MEDICINE of Federal Way, Wash. or THE AMERICAN ACADEMY OF ANTI AGING MEDICINE of Boca Raton, Fla. A standard may be based on various approaches to medicine including for example conventional medicine approaches, functional medicine approaches, Western medical practices, Eastern medical practices, and/or any combination of the above. For instance and without limitation, a standard may include treating initial primary hypertension with lifestyle treatments including a fitness routine and nutritional treatments to remote excess sodium from one's diet. In yet another non-limiting example, a standard may include treating a systemic *candida* infection with anti-fungal medications in addition to dietary modifications that include initiating a grain free and refined sugar free diet. An "implementation factor," as used in this disclosure, is a factor that indicates a user preference for different treatment practices. An implementation factor 172 may indicate if a user likes and/or dislikes different categories of treatments. For example, a user may prefer dietary treatments over prescriptive treatments or fitness treatments over medical procedures. One or more implementation factor 172 pertaining to a user may be received from a remote device 132 operated by a user and stored in user database 120. A "corrective factor," as used in this disclosure, is a factor that indicates the intensity of a treatment. Intensity may include how soon a treatment needs to be implemented, how rigorous a course of treatment needs to be, the length of a particular treatment, and time commitment a user needs to devote to a treatment. For example, a corrective factor 176 may indicate that a treatment such as a surgical intervention needs to be performed immediately, while a treatment such as a fitness program will be implemented over the course of the next six months.

With continued reference to FIG. 1, computing device 104 may select a treatment training set 152 and a treatment model 156 based on user input. Computing device 104 may receive from a remote device 132 a user entry containing a current treatment input descriptor 180. A "current treatment input descriptor," as used in this disclosure, is a description of any treatment a user may be currently practicing and/or prescribed. A current treatment input descriptor 180 may include a description of the treatment a user is currently practicing and has been prescribed, the frequency in which the user practices the treatment, the intensity, the time commitment, and the like. A current treatment input descriptor 180 may include a description of a prescription medication a user may be taking twice daily for hypertension. A current treatment input descriptor 180 may include a description of a fitness regimen that a user engages in to lose weight. A current treatment input descriptor 180 may include a description of a meditation practice that a user practices to combat a user's anxiety. Computing device 104 utilizes a current treatment input descriptor 180 to locate treatment training data and/or a treatment model 156. In an embodiment, treatment training data and/or a treatment model 156 may be categorized according to various classification schemes such as intensity levels, what condition state label 116 that are intended for, what role they play in treatment, when they should be implemented and the like. Computing device 104 may compare a current treatment input descriptor 180 to treatment training data and/or treatment model 156 to select related treatments, to select a related treatment, to select a higher or lower intensity treatment and the like. For instance and without limitation, a current treatment input descriptor 180 that includes a description of a user's current treatment that describes a user engages in yoga three times each week to improve a user's strength and flexibility may be utilized by computing device 104 to select a treatment training set 152 and/or treatment model 156 that contains a fitness treatment that includes yoga. In yet another non-limiting example, a current treatment input descriptor 180 that includes a user's current treatment as a prescription medication to reduce user's high cholesterol may be utilized by computing device 104 to select a treatment training set 152 and/or treatment model 156 that implements prescription medication treatments with dietary treatments.

With continued reference to FIG. 1, computing device 104 is configured to generate using a machine-learning algorithm, a condition state label 116 and the selected treatment training set 152 a treatment model 156.

With continued reference to FIG. 1, computing device 104 is configured to output a plurality of treatments utilizing the treatment model 156. In an embodiment, computing device 104 may display one or more treatments on a graphical user interface 184 located on computing device 104. Graphical user interface 184 may include without limitation a form or other graphical element having display fields, where one or more treatments may be displayed to a user. In an embodiment, computing device 104 may transmit a plurality of output treatments to a remote device 132 operated by a user and/or a user's informed advisor. For instance and without limitation, computing device 104 may transmit a plurality of output treatments to a user's functional medicine doctor or spiritual coach.

With continued reference to FIG. 1, computing device 104 may select a treatment from the plurality of output treatments by generating a loss function. Computing device 104 may utilize a loss function analysis utilizing linear regression to select a treatment from a plurality of output treatments. A "loss function," as used in this disclosure, is an expression of an output of which an optimization algorithm minimizes to generate an optimal result. As a non-limiting example, computing device 104 may calculate variables based on a user input regarding various variables relating to treatments, calculate an output of mathematical expression using the variables, and select an element that produces an output having the lowest size, according to a given definition of "size," of the sets of outputs representing each of the plurality of elements; size may, for instance, include absolute value, numerical size, or the like. Selection of different loss function may result in identification of different elements as generating minimal outputs; for instance, wherein a variable such as time commitment is associated in a first loss function with a large coefficient or weight, a variable such as cost having a small coefficient or weight may minimize the first loss function, whereas a second loss function where time commitment has a smaller coefficient but degree of variance from cost may produce a minimal output for a different variable having a larger coefficient for cost but more closely hewing to time commitment.

With continued reference to FIG. 1, mathematical expression and/or loss function may be generated using a machine learning to produce loss function: i.e., regression. Mathematical expression and/or loss function be user-specific, using a training set composed of previous user variables; which may be updated continuously. "User variables," as used in this disclosure, are any current and/or previously entered user inputs regarding treatments. User variables may include inputs regarding how much money a user is willing to spend on treatment, how far a user is willing to travel for treatment, how long a user is willing to devote to treatment and the like. Mathematical expression and/or loss function may initially be seeded using one or more variables as described above. User may enter a new command changing mathematical expression, and then subsequent user selections may be used to generate a new training set to modify the new expression.

With continued reference to FIG. 1, mathematical expression and/or loss function may be generated using machine learning using a multi-user training set. Training set may be created using data of a cohort of persons having similar demographic, religious, health, lifestyle characteristics, and/or variable rankings to user. This may alternatively or additionally be used to seed a mathematical expression and/or loss function for a user, which may be modified by further machine learning and/or regression using subsequent selection variables. Computing device 104 minimizes a loss function and selects a treatment from the plurality of output treatments for a user as a result of minimizing a loss function.

With continued reference to FIG. 1, computing device 104 may compare one or more user variables to a mathematical expression representing an optimal combination of user variable rankings. Mathematical expression may include a linear combination of variables, weighted by coefficients representing relative importance of each variable in selecting an optimal treatment. For instance, a variable such as treatment intensity may be multiplied by a first coefficient representing the importance of treatment intensity, a second variable such as cost may be multiplied by a second coefficient representing the importance of cost, a third variable may be multiplied by a third coefficient representing the importance of that variable; persons skilled in the art, upon reviewing the entirety of this disclosure, will be aware of different variables that may be weighted by various coefficients. Use of a linear combination is provided only as an illustrative example; other mathematical expressions may alternatively or additionally be used, including without limitation higher-order polynomial expressions or the like. Variables may include one or more user responses in regard to different treatment options. Variables may indicate for example, how much money a user is willing to spend on a treatment, how much time a user is willing to devote to a treatment, how complex of a treatment a user is willing to partake in, how intense of a treatment a user is interested in partaking, previous treatments, treatments that a user enjoyed, treatments that a user did not enjoy, treatments a user is able to partake in, treatments a user is unable to partake in, and the like.

With continued reference to FIG. 1, each user entry relating to a particular variable may be represented by a mathematical expression having the same form as mathematical expression; computing device 104 may compare the former to the latter using an error function representing average difference between the two mathematical expressions. Error function may, as a non-limiting example, be calculated using the average difference between coefficients corresponding to each input variable. A variable ranking having a mathematical expression minimizing the error function may be selected, as representing an optimal expression of relative importance of variables to a system or user. In an embodiment, error function and loss function calculations may be combined; for instance, a user entry ranking resulting in a minimal aggregate expression of error function and loss function, such as a simple addition, arithmetic mean, or the like of the error function with the loss function, may be selected, corresponding to an option that minimizes total variance from optimal variables while simultaneously minimizing a degree of variance from a set of priorities corresponding to additional variables. Coefficients of mathematical expression and/or loss function may be scaled and/or normalized; this may permit comparison and/or error function calculation to be performed without skewing by varied absolute quantities of numbers.

Still referring to FIG. 1, mathematical expression and/or loss function may be provided by receiving one or more user commands. For instance, and without limitation, a graphical user interface 184 may be provided to user with a set of sliders or other user inputs permitting a user to indicate relative and/or absolute importance of each variable containing a user entry ranking to the user. Sliders or other inputs may be initialized prior to user entry as equal or may be set to default values based on results of any machine-learning processes or combinations thereof as described in further detail below. One or more user entries relating to variables may be stored in user database 120.

With continued reference to FIG. 1, computing device 104 is configured to utilize generated outputs to updated training data sets and/or models contained within system 100. Computing device 104 may utilize an output plurality of treatments and a user biological extraction 108 to incorporate them into a subsequent training set. Computing device 104 may utilize an output condition state label 116 generated for an element of user physiological data, and an element of user physiological data to update condition state training data 112. Computing device 104 may incorporate one or more updated training sets and/or machine-learning models to be stored within machine-learning database 124.

Figure 2:
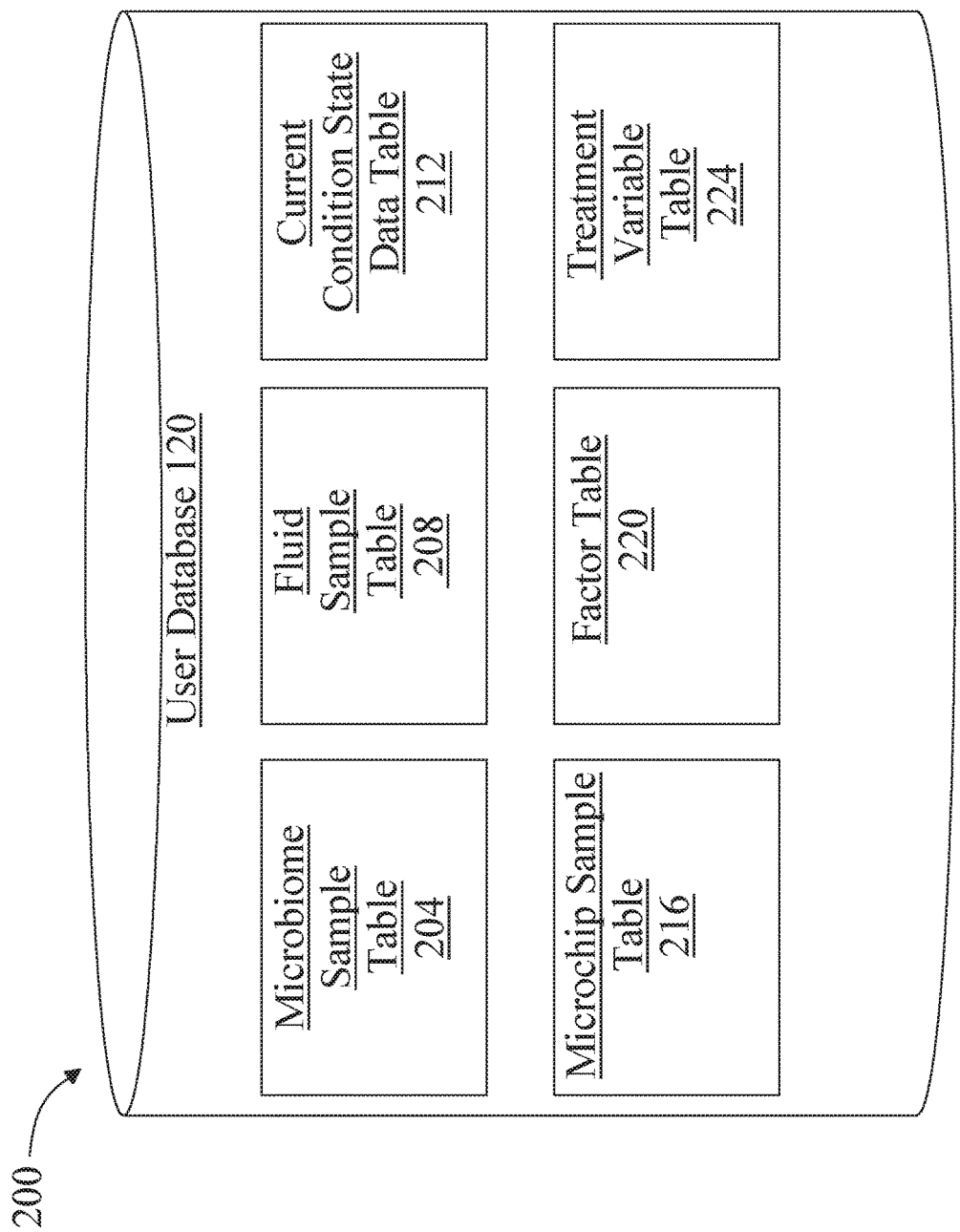
FIG. 2 is a block diagram illustrating an exemplary embodiment of a user database.

Referring now to FIG. 2, an exemplary embodiment of user database 120 is illustrated. User database 120 may be implemented as any data structure as described above in more detail. One or more tables contained within user database 120 may include microbiome sample table 204; microbiome sample table 204 may include one or more biological extraction 108 relating to the microbiome. For instance and without limitation, microbiome sample table 204 may include a physically extracted sample such as a stool sample analyzed for the presence of pathogenic species such as parasites and anaerobes. One or more tables contained within user database 120 may include fluid sample table 208; fluid sample table 208 may include one or more biological extraction 108 containing fluid samples. For instance and without limitation, fluid sample table 208 may include a urine sample analyzed for the presence or absence of glucose. One or more tables contained within user database 120 may include current condition state data table 212; current condition state 136 data table 212 may include one or more current conditions and/or treatments pertaining to a user. For instance and without limitation, current condition state data table 212 may include a user's previous diagnosis of a chronic medical condition such as rheumatoid arthritis and a current treatment the user engages in to control symptom such as a series of meditative poses. One or more tables contained within user database 120 may include microchip sample table 216; microchip sample table 216 may include one or more biological extractions obtained from a microchip. For instance and without limitation, microchip sample table 216 may include an intracellular nutrient level obtained from a microchip embedded under a user's skin. One or more tables contained within user database 120 may include factor table 220; factor table 220 may include one or more factors utilized to calculate a treatment category selector 160. For instance and without limitation, factor table 220 may include one or more approach factors 168, implementation factors 172, and/or corrective factors 176. One or more tables contained within user database 120 may include treatment variable table 224; treatment variable table 224 may include one or more user responses to one or more treatment variables. For instance and without limitation, treatment variable table 224 may include a user response generated in regard to the cost of a treatment.

Figure 3:
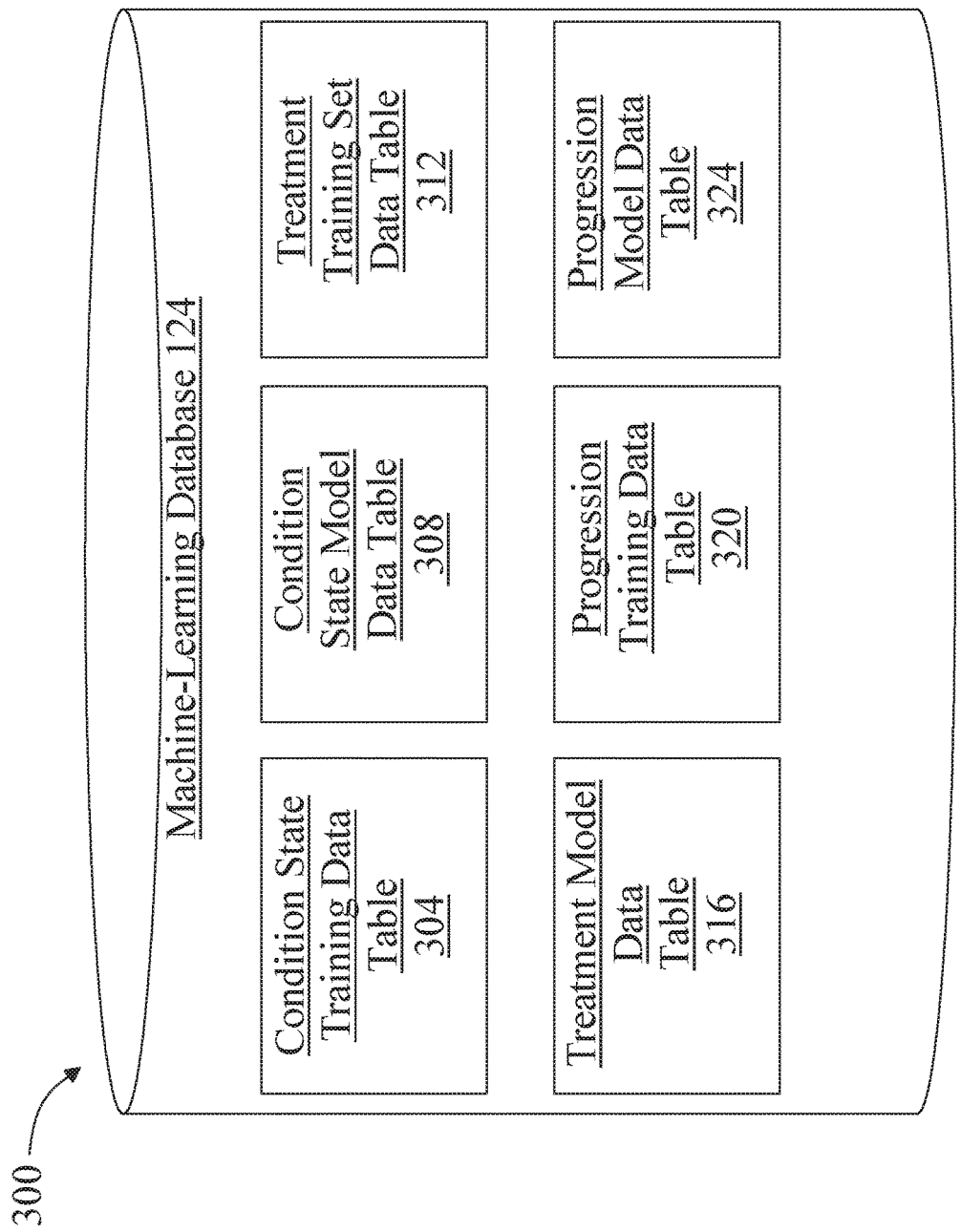
FIG. 3 is a block diagram illustrating an exemplary embodiment of a machine-learning database.

Referring now to FIG. 3, an exemplary embodiment of machine-learning database 124 is illustrated. Machine-learning database 124 may be implemented as any data structure suitable for use as user database 120 as described above in more detail. One or more tables contained within machine-learning database 124 may include condition state training data table 304; condition state training data table 304 may include one or more condition state training data 112 sets. One or more tables contained within machine-learning database 124 may include condition state model data table 308; condition state model data table 308 may include one or more condition state model 128. One or more tables contained within machine-learning database 124 may include treatment training set data table 312; treatment training set data table 312 may include one or more treatment training set 152. One or more tables contained within machine-learning database 124 may include treatment model data table 316; treatment model data table 316 may include one or more treatment model 156. One or more tables contained within machine-learning database 124 may include progression training data table 320; progression training data table 320 may include one or more progression training data 144 sets. One or more tables contained within machine-learning database 124 may include progression model data table 324; progression model data table 324 may include one or more progression models 148. In an embodiment, training sets and/or machine-learning models contained within machine-learning database 124 may be organized according to one or more categories such as for example, by condition, by treatment, by severity of condition, by progression of condition and the like. One or more machine-learning models contained within machine-learning database 124 may have been previously calculated.

Figure 4:
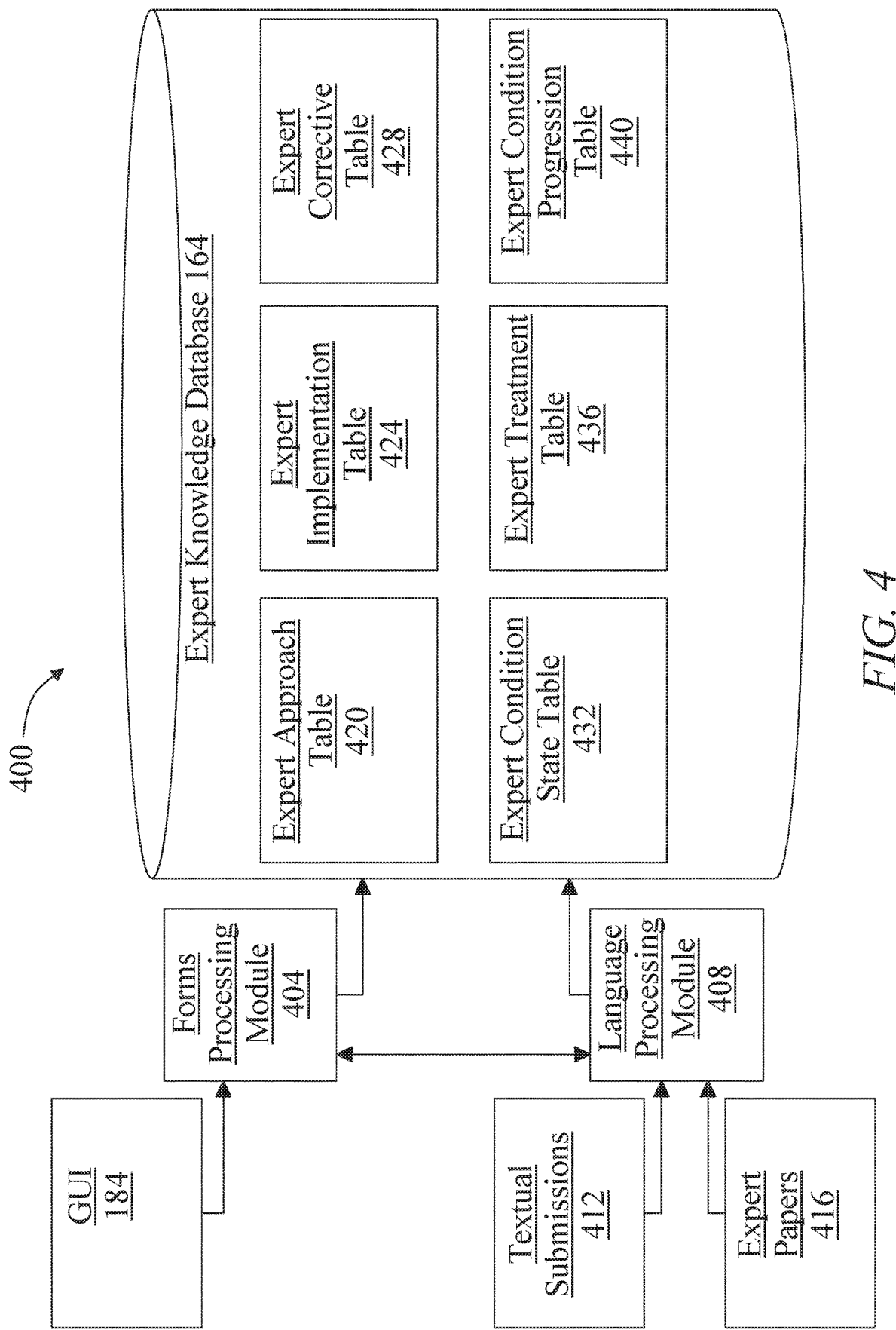
FIG. 4 is a block diagram illustrating an exemplary embodiment of an expert knowledge database.

Referring now to FIG. 4, an exemplary embodiment 400 of expert knowledge database 164 is illustrated. Expert knowledge database 164 may be implemented as any data structure suitable for use as user database 120 as described above in reference to FIG. 1. One or more database tables may be linked to one another by, for instance, common column values. For instance, a common column between two tables of expert knowledge database 164 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data may be included in one or more tables.

With continued reference to FIG. 4, expert knowledge database 164 includes a forms processing module 404 that may sort data entered in a submission via graphical user interface 184 by, for instance, sorting data from entries in the graphical user interface 184 to related categories of data; for instance, data entered in an entry relating in the graphical user interface 184 to a treatment may be sorted into variables and/or data structures for storage of treatments, while data entered in an entry relating to a category of condition state label 116 and/or an element thereof may be sorted into variables and/or data structures for the storage of, respectively, categories of condition state label 116. Where data is chosen by an expert from pre-selected entries such as drop-down lists, data may be stored directly; where data is entered in textual form, language processing module 408 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module 408 may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 412, such as accomplished by filling out a paper or PDF form and/or submitting narrative information, may likewise be processed using language processing module 408. Data may be extracted from expert papers 416, which may include without limitation publications in medical and/or scientific journals, by language processing module 408 via any suitable process as described herein. Persons skilled in the art, upon reviewing the entirety of this disclosure, will be aware of various additional methods whereby novel terms may be separated from already-classified terms and/or synonyms therefore, as consistent with this disclosure.

Figure 5:
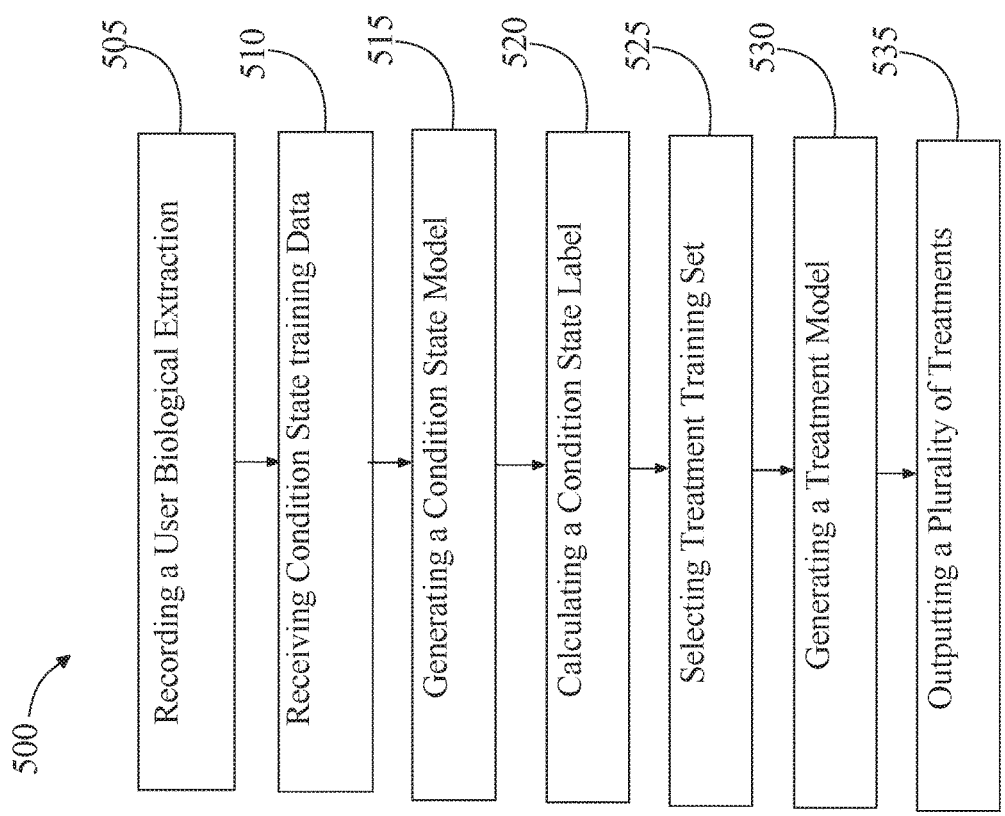
FIG. 5 is a process flow diagram illustrating an exemplary embodiment of a method of customizing treatments.

With continued reference to FIG. 5, one or more tables contained within expert knowledge database 164 may include expert approach table 420; expert approach table 420 may include one or more data entries containing expert input regarding approach factor 168. One or more tables contained within expert knowledge database 164 may include expert implementation table 424; expert implementation table 424 may include one or more data entries containing expert input regarding implementation factor 172. One or more tables contained within expert knowledge database 164 may include expert corrective table 428; expert corrective table 428 may include one or more data entries containing expert input regarding corrective factor 176. One or more tables contained within expert knowledge database 164 may include expert condition state table 432; expert condition state table 432 may include one or more data entries containing condition states and physiological data. One or more tables contained within expert knowledge database 164 may include expert treatment table 436; expert treatment table 436 may include one or more data entries containing expert input regarding treatments for condition states. One or more tables contained within expert knowledge database 164 may include expert condition progression table 440; expert condition progression table 440 may include one or more data entries containing expert input regarding condition progression.

Referring now to FIG. 5, an exemplary embodiment of a method 500 of customizing treatments is illustrated. At step 505, a computing device 104 records a user biological extraction 108 containing an element of user physiological data. A user biological extraction 108 includes any of the user biological extractions as described above in reference to FIGS. 1-4. For instance and without limitation, a biological extraction 108 may include a blood sample analyzed for a user's intracellular nutrient levels. In yet another non-limiting example, a biological extraction 108 may include an element of user psychological data such as for example, a user response regarding a user's current mood and mental state. An element of user physiological data includes any of the elements of user physiological data as described above in reference to FIGS. 1-4.

With continued reference to FIG. 5, at step 510 a computing device 104 receives condition state training data 112. Condition state training data 112 includes any of the condition state training data 112 as described above in reference to FIGS. 1-4. Condition state training data 112 includes a plurality of physiological data sets and a plurality of correlated condition state label 116. In an embodiment, condition state training data 112 may be retrieved from machine-leaning database. In an embodiment, condition state training data 112 The system of claim 1, wherein receiving condition state training data 112 may be generated from a plurality of user data entries such as from previously recorded user biological extraction 108 and previously calculated condition state label 116 utilizing system 100. In such an instance, condition state training data 112 may include a plurality of user physiological data sets and a plurality of correlated user condition state label 116.

With continued reference to FIG. 5, at step 515 a computing device 104 generates a condition state model 128, using the element of user physiological data and the condition state training data 112, and using a first machine-learning algorithm. Condition state model 128 includes any of the condition state model 128 as described above in reference to FIGS. 1-4. Condition state model 128 utilizes physiological data as inputs and outputs condition state label 116. First machine-learning algorithm includes any of the machine-learning algorithms as described above. This may include for example generating one or more supervised machine-learning algorithms, one or more unsupervised machine-learning algorithms, and/or one or more lazy-learning algorithms. Selection of a particular machine-learning algorithm may be based on one or more expert inputs such as for example expert input contained within expert knowledge database 164.

With continued reference to FIG. 5, at step 520 a computing device 104 calculates a condition state label 116 for the element of user physiological data using the condition state model 128 and the element of user physiological data. Condition state label 116 includes any of the condition state label 116 as described above in reference to FIGS. 1-4. In an embodiment, a condition state label 116 describes a current, incipient, or probable future medical condition affecting a human being. For instance and without limitation, a condition state label 116 may describe a probable future medical condition such as myocardial infarction based on a user's elevated total cholesterol, elevated low density lipoprotein (LDL), dangerously low high density lipoprotein (HDL), and a positive confirmation of a medical procedure showing 90% blockage of a coronary artery. Computing device 104 may calculate a condition state label 116 to contain a current condition state progression indicator 140. Current condition state progression indicator 140 may include any of the current condition state 136 progression indicators as described above in reference to FIGS. 1-4. Current condition state progression indicator 140 may reflect how far progressed a current condition state 136 is. For instance and without limitation, a current condition state progression indicator 140 may report that a condition state such as ulcerative colitis has advanced to causing systemic complications that include sore joints and headaches. In yet another non-limiting example, a current condition state 136 progression indicator may reflect that an acute condition such as a urinary tract infection has been completely resolved following consumption of cranberry extract and d-mannose for six days. Computing device 104 may utilize a current condition state progression indicator 140 to select a treatment training set 152 and a treatment training model. In an embodiment, a treatment training set 152 and/or treatment training model may be organized within machine-learning database 124 based on progression of condition states contained within treatment training set 152 and/or treatment training models, and computing device 104 may match a current condition state progression indicator 140 to a proportionate treatment training set 152 and/or treatment training model. In an embodiment, treatment training set 152 and/or treatment training models may contain condition state progression indicator labels that indicate the progression of condition states contained within treatment training set 152 and/or treatment training models to match condition state progression indicator labels to condition state progression indicators.

With continued reference to FIG. 5, condition state progression indicator may be generated utilizing one or more machine-learning processes. Computing device 104 receives progression training data 144. Progression training data 144 includes any of the progression training data 144 as described above in reference to FIGS. 1-4. Progression training data 144 includes a plurality of physiological data sets and a plurality of correlated progression indicators. Computing device 104 generates a progression model 148 using a machine-learning algorithm, the element of user physiological data, and the progression training data 144. Progression model 148 utilizes physiological data as inputs and outputs progression indicators. Progression model 148 may be generated utilizing any of the methodologies as described above in reference to FIGS. 1-4. Computing device 104 calculates a condition state progression indicator utilizing the progression model 148.

With continued reference to FIG. 5, at step 525 computing device 104 selects a treatment training set 152 and a treatment model 156 utilizing the condition state label 116. Treatment training set 152 includes any of the treatment training set 152 as described above in reference to FIGS. 1-4. Treatment training set 152 includes a plurality of condition state label 116 and a plurality of correlated treatments. Computing device 104 may select a treatment training set 152 and/or treatment model 156 by matching an output condition state label 116 to a treatment training set 152 and/or treatment model 156 that contains the same condition state label 116. For instance and without limitation, an output condition state label 116 such as open angle glaucoma may be matched to a treatment training set 152 and/or treatment model 156 intended for open angle glaucoma. In an embodiment, treatment training set 152 and/or treatment model 156 may be stored within machine-learning database 124 according to condition state. Computing device 104 may select a treatment training set 152 and/or treatment model 156 by calculating a treatment category selector 160 and selecting a treatment training set 152 and/or treatment model 156 related to the treatment category selector 160. Treatment category selector 160 includes any of the treatment category selectors as described above in reference to FIGS. 1-4. Treatment category selector 160 includes an indication as to a particular category of treatment to be implemented and/or recommended for a particular condition identified from a condition state label 116. For instance and without limitation, a treatment category selector 160 may indicate that a condition such as metabolic syndrome is to be treated with behavior modifications and nutritional treatments. In yet another non-limiting example, a treatment category selector 160 may indicate that a condition such as pulmonary hypertension is to be treated with medication treatments and fitness treatments. Computing device 104 may select a treatment training set 152 and a treatment model 156 related to a treatment category selector 160. For instance and without limitation, computing device 104 may select a treatment training set 152 that contains treatment outputs that are of the same category of treatment contained within a treatment category selector 160. For example, computing device 104 may utilize a treatment category selector 160 that contains nutritional treatments and homeopathic treatments to select a treatment training set 152 and a treatment model 156 that contains nutritional treatments and/or homeopathic treatments. Computing device 104 may calculate treatment category selector 160 by multiplying an approach factor 168 multiplied by an implementation factor 172 multiplied by a corrective factor 176. Factors utilized to calculate treatment category selector 160 may contain numerical values that may be utilized to select an output containing a treatment training set 152 and/or treatment model 156. This may be performed as described above in more detail in reference to FIG. 1. Computing device 104 may select a treatment training set 152 and/or a treatment model 156 based on a current treatment input descriptor 180 received from a remote device 132. Current treatment input descriptor 180 includes any of the current treatment input descriptor 180 as described above in reference to FIGS. 1-4.

In an embodiment, current treatment input descriptor 180 may include a description of one or more current treatments the user may be currently practicing and/or implementing. Current treatment input descriptor 180 may be received by computing device 104 from a remote device 132 operated by a user utilizing any network methodology and transmission as described herein. Computing device 104 may locate a treatment training set 152 and/or treatment model 156 as a function of a current treatment input descriptor 180. For example, computing device 104 may locate a treatment model 156 that contains output treatments that further expand and/or build upon treatments a user may be currently engaging in. For example, computing device may select a treatment model 156 that contains additional exercises that increase flexibility for a user who is currently practicing yoga three times each week. In an embodiment, computing device 104 may utilize a current treatment input descriptor 180 to select additional categories of treatment that a user may implement. For example, computing device 104 may select a treatment model 156 that contains additional treatment categories such as dietary treatments and behavior modifications for a user who is currently engaged in prescription therapies.

With continued reference to FIG. 5, at step 530, computing device 104 generates a treatment model 156 utilizing a machine-learning algorithm, a condition state label 116 and selected treatment training data. Computing device 104 may generate a treatment model 156 utilizing any of the methodologies as described above in reference to FIGS. 1-4. Generating treatment model 156 may include calculating one or more machine-learning algorithms. Machine-learning algorithms include any of the machine-learning algorithms as described above in reference to FIGS. 1-4. Treatment model 156 utilizes a condition state label 116 as an input and outputs a plurality of treatments. Treatments include any of the treatments as described above in reference to FIGS. 1-4.

With continued reference to FIG. 5, at step 535, computing device 104 outputs a plurality of treatments utilizing the treatment model 156. Treatments include any of the treatments as described above in reference to FIGS. 1-4. Computing device 104 may select a treatment from the plurality of output treatments by generating a loss function. Computing device 104 may receive user variables from a remote device 132 operated by a user relating to the plurality of output treatments. Variables may include one or more user responses in regard to different aspects of treatment. For example, variables may include one or more user views regarding cost which may indicate how much money a user is willing to spend on a particular treatment. Variables may include other user inputs regarding treatments such as how much time each day a user is willing to devote to a treatment, how adherent a user is with previous treatments, how far a user is willing to travel to receive treatment, how intense of treatment a user seeks to engage in, a user's views on functional medicine treatments versus conventional treatments and the like. Computing device 104 may utilize variables to generate a loss function utilizing the user variables and minimize the loss function. This may be performed utilizing any of the methodologies as described above in reference to FIGS. 1-4. Computing device 104 selects a treatment from a plurality of output treatments as a function of minimizing the loss function.

With continued reference to FIG. 1, computing device 104 may utilize generated inputs and outputs in machine-learning models and/or machine-learning algorithms to update subsequent uses of system 100. Computing device 104 incorporates output treatments and a user biological extraction 108 into a treatment training set 152. In an embodiment, an updated treatment training set 152 that contains output treatments and a user biological extraction 108 may be stored in machine-learning database 124 to be utilized in subsequent machine-learning algorithms and models. Computing device 104 may incorporate a condition state label 116 generated for an element of user physiological data into condition state training data 112. In an embodiment, computing device 104 may incorporate an element of user physiological data and a generated conditions state label into condition state training data 112. Updated training sets may be sorted within machine-learning database 124.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
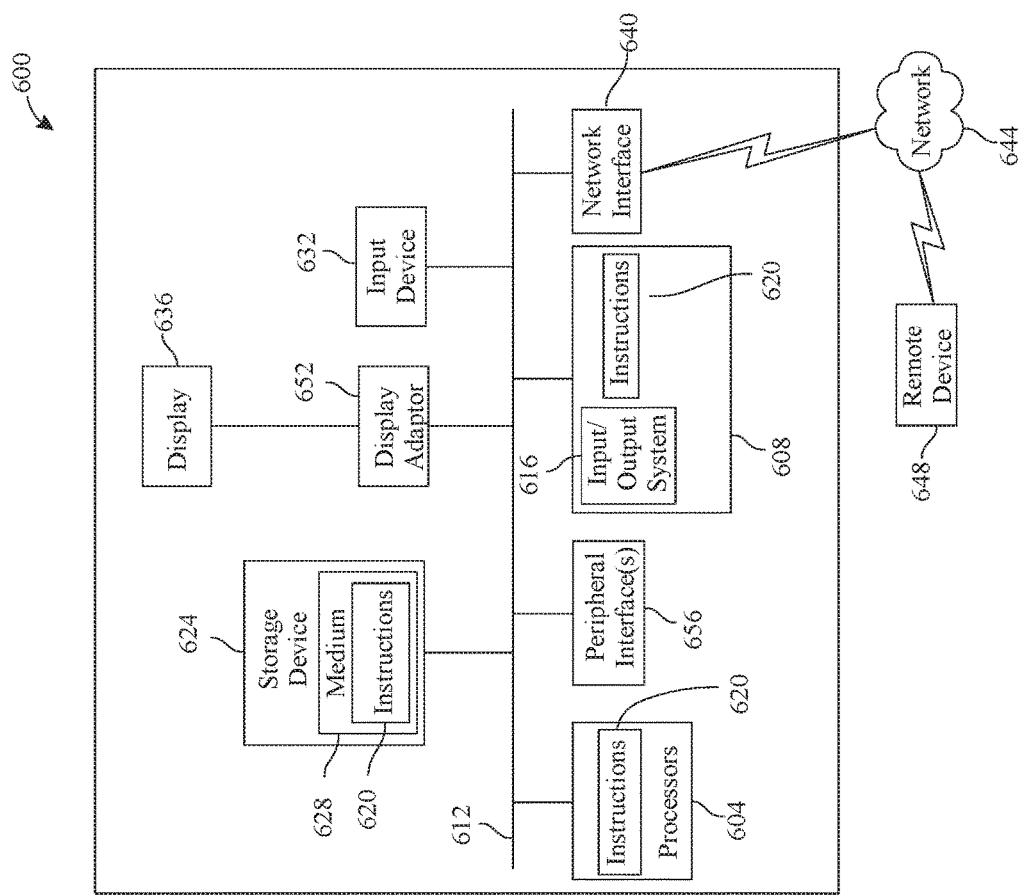
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Memory 608 may include various components (e.g., machine-readable media) including, but not limited to, a random access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIRE-WIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote device 132 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for customizing treatments, the system comprising:
a computing device, the computing device designed and configured to:
record a user biological extraction containing an element of user physiological data;
generate a condition state model, wherein the condition state model comprises a first machine-learning model trained by condition state training data comprising a plurality of physiological data sets and a plurality of correlated condition state labels, wherein the condition state model is configured to receive the element of user physiological data as an input and output a condition state label associated with the element of user physiological data, wherein the computing device is configured to utilize an outputted condition state label to update condition state training data;
calculate a current condition state progression indicator, wherein calculating the current condition state progression indicator further comprises:
generating a progression model, wherein the progression model comprises a second machine-learning model trained by progression training data comprising a plurality of physiological data sets and a plurality of correlated progression indicators and wherein the progression model is configured to receive the element of user physiological data as an input and output a current condition state progression indicator;
select a treatment training set according to the condition state label associated with the element of user physiological data and the current condition state progression indicator, wherein the treatment training set further comprises a plurality of condition state labels and a plurality of correlated treatments; and
generate a treatment model, wherein the treatment model comprises a third machine-learning model trained by the selected treatment training set and wherein the treatment model is configured to receive the condition state label associated with the element of user physiological data as an input and output a plurality of treatments, and wherein generating the treatment model further comprises:
calculating a treatment category selector, wherein calculating the treatment selector comprises an approach factor, multiplied by an implementation factor, multiplied by a corrective factor, wherein the implementation factor is a factor that indicates a user preference pertaining to different treatment practices; and
selecting the treatment training set further according to the treatment category selector.

2. The system of claim 1, wherein the computing device is further configured to receive previously collected user data and generate the condition state training data, wherein the condition state training data further includes a plurality of physiological data obtained from user entries and a plurality of correlated user condition state labels obtained from user entries.

3. The system of claim 1, wherein the computing device is further configured to:
receive, from a remote device, a description of a current condition state, wherein the condition state model is further configured to receive the description of a current condition state as an input and output a current condition state progression indicator, and wherein the treatment training set is further selected according to the current condition state progression indicator.

4. The system of claim 1, wherein selecting the treatment training set further comprises:
receiving from a remote device a user entry containing a current treatment input descriptor; and
locating a potential treatment model as a function of the current treatment input descriptor.

5. The system of claim 1, wherein the computing device is further configured to:
receive, from a remote device operating by a user, user variables relating to the plurality of treatments;
generating a loss function utilizing the user variables;
minimizing the loss function;
selecting a treatment from the plurality of treatments as a function of minimizing the loss function; and
outputting the selected treatment.

6. The system of claim 1, wherein the plurality of treatments and the user biological extraction are incorporated into the treatment training set.

7. The system of claim 1, wherein the implementation factor indicates if a user likes or dislikes a first category of treatment over a second category of treatment.

8. The system of claim 7, wherein the implementation factor indicates that the user prefers a dietary treatment over a prescriptive treatment or a fitness treatment.

9. The system of claim 8, wherein the implementation factor indicates that the user prefers the prescriptive treatment or the fitness treatment over a medical procedure.

10. A method of customizing treatments, the method comprising:
recording, by a computing device, a user biological extraction containing an element of user physiological data;
generating, by the computing device, a condition state model, wherein the condition state model comprises a first machine-learning model trained by condition state training data comprising a plurality of physiological data sets and a plurality of correlated condition state labels, wherein the condition state model is configured to receive the element of user physiological data as an input and output a condition state label associated with the element of user physiological data, wherein the computing device is configured to utilize an outputted condition state label to update condition state training data;
calculating, by the computing device, a current condition state progression indicator, wherein calculating the current condition state progression indicator further comprises:
generating a progression model wherein the progression model comprises a second machine-learning model trained by progression training data comprising a plurality of physiological data sets and a plurality of correlated progression indicators and wherein the progression model is configured to receive the element of user physiological data as an input and output a current condition state progression indicator;

selecting, by the computing device, a treatment training set according to the condition state label associated with the element of user physiological data, wherein the treatment training set further comprises a plurality of condition state labels and a plurality of correlated treatments; and generating, by the computing device, a treatment model, wherein the treatment model comprises a third machine-learning model trained by the selected treatment training set and wherein the treatment model is configured to receive the condition state label associated with the element of user physiological data as an input and output a plurality of treatments, wherein generating the treatment model further comprises:

calculating a treatment category selector, wherein calculating the treatment selector comprises an approach factor, multiplied by an implementation factor, multiplied by a corrective factor, wherein the implementation factor is a factor that indicates a user preference pertaining to different treatment practices; and selecting the treatment training set further according to the treatment category selector.

11. The method of claim 10, further comprising:
receiving previously collected user data; and
generating the condition state training data, wherein the condition state training data further includes a plurality of physiological data obtained from user entries and a plurality of correlated user condition state labels obtained from user entries.

12. The method of claim 10, further comprising:
receiving from a remote device a description of a current condition state, wherein the condition state model is further configured to receive the description of current condition state as an input and output a current condition state progression indicator, and wherein the treatment training set is further selected according to the current condition state progression indicator.

13. The method of claim 10, wherein selecting the treatment training set further comprises:
receiving from a remote device a user entry containing a current treatment input descriptor; and
locating a potential treatment model as a function of the current treatment input descriptor.

14. The method of claim 10, further comprising:
receiving, from a remote device operating by a user, user variables relating to the plurality of treatments;
generating a loss function utilizing the user variables;
minimizing the loss function;
selecting a treatment from the plurality of treatments as a function of minimizing the loss function; and
outputting the selected treatment.

15. The method of claim 10 further comprising incorporating the plurality of treatments and the user biological extraction into the treatment training set.

16. The method of claim 10, wherein the implementation factor indicates if a user likes or dislikes a first category of treatment over a second category of treatment.

17. The method of claim 16, wherein the implementation factor indicates that the user prefers a dietary treatment over a prescriptive treatment or a fitness treatment.

18. The method of claim 17, wherein the implementation factor indicates that the user prefers the prescriptive treatment or the fitness treatment over a medical procedure.

* * * * *